(12) United States Patent
Jansen

(10) Patent No.: US 7,959,948 B2
(45) Date of Patent: Jun. 14, 2011

(54) PHARMACEUTICAL COMPOSITION OF QUETIAPINE FUMARATE

(75) Inventor: Korinde Annemarie Jansen, Beuningen (NL)

(73) Assignee: Synthon BV, Nijmegen (NL)

( * ) Notice: Subject to any disclaimer, the term of this patent is extended or adjusted under 35 U.S.C. 154(b) by 302 days.

(21) Appl. No.: 12/044,706

(22) Filed: Mar. 7, 2008

(65) Prior Publication Data

US 2008/0221079 A1    Sep. 11, 2008

Related U.S. Application Data

(60) Provisional application No. 60/894,064, filed on Mar. 9, 2007.

(51) Int. Cl.
*A61K 31/554* (2006.01)
*A61P 25/18* (2006.01)

(52) U.S. Cl. .................................. 424/486; 514/211.01

(58) Field of Classification Search .................... 424/486
See application file for complete search history.

(56) References Cited

U.S. PATENT DOCUMENTS

2004/0005360 A1*  1/2004  Wang et al. ................... 424/473
2005/0158383 A1*  7/2005  Boehm et al. ................. 424/468

FOREIGN PATENT DOCUMENTS

| EP | 0 240 228 A1 | 10/1987 |
|---|---|---|
| WO | WO 97/45124 | 12/1997 |
| WO | WO 2004/078735 A1 | 9/2004 |
| WO | WO 2005/041935 A1 | 5/2005 |

OTHER PUBLICATIONS

Dr. Bernhard Fussnegger. Kollidon SR: A polyvinyl acetate based excipient for DC-sustained-release oral dosage forms. pp. 1-6. Avalaible online via the wayback machine as of Jul. 16, 2004. http://www.iptonline.com/articles/public/IPTOLARTBASFNP.pdf archived: http://web.archive.org/web/*/http://www.iptonline.com/articles/public/IPTOLARTBASFNP.pdf.*
Signet  http://www.signetchem.com/Signet-The-Complete-Excipients-Company-Product-Kollidon-SR.*
Signet  http://www.signetchem.com/Signet-The-Complete-Excipients-Company-Product-Kollidon-SR. Mar. 2010.*

* cited by examiner

*Primary Examiner* — Shanon A. Foley
*Assistant Examiner* — Sarah Al-Awadi
(74) *Attorney, Agent, or Firm* — Muncy, Geissler, Olds & Lowe, PLLC

(57) ABSTRACT

A pharmaceutical composition comprising (i) quetiapine or a pharmaceutically acceptable salt thereof, especially quetiapine fumarate; (ii) a mixed excipient comprising an intimate admixture of polyvinylacetate and polyvinylpyrrolidone in a weight ratio from 5:2 to 10:2; and, optionally (iii) an acid especially fumaric acid.

17 Claims, No Drawings

PHARMACEUTICAL COMPOSITION OF QUETIAPINE FUMARATE

This application claims the benefit under 35 U.S.C. §119(e) of U.S. Provisional Patent Application No. 60/894,064, filed Mar. 9, 2007, the entire contents of which are incorporated herein by reference.

BACKGROUND OF THE INVENTION

The present invention relates to a controlled release dosage form containing quetiapine or its salt especially quetiapine fumarate.

Quetiapine, 2-[2-(4-dibenzo[b,f] [1,4] thiazepin-11-yl-1-piperazinyl)ethoxy]ethanol of the formula (I):

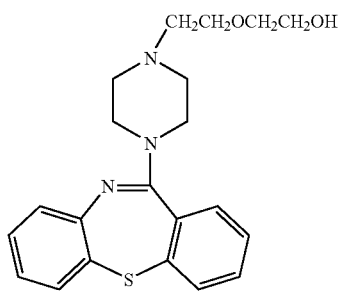

is an antipsychotic agent indicated for treatment of various types of psychoses.

The quetiapine compound as well as the fumarate salt thereof have been disclosed, e.g., in EP 240228. The patent application WO 2004/078735 disclosed various crystalline polymorphs of quetiapine fumarate, particularly crystalline polymorph Form I, Form II, and an amorphous product.

As a pharmaceutical drug, quetiapine is marketed as quetiapine fumarate (technically a hemifumarate salt, i.e., a 2:1 molar ratio of base to acid ion). It is a white crystalline powder (m.p. 172-173° C.) that is moderately soluble in water. It is sold under the brand name SEROQUEL® (AstraZeneca), e.g. within a pharmaceutical tablet comprising from 25 to 400 mg of the quetiapine fumarate, calculated as the free base. Inactive ingredients are listed (see, for instance, Rote Liste 2003) as povidone, calcium hydrogen phosphate dihydrate, microcrystalline cellulose, sodium starch glycolate, lactose monohydrate, magnesium stearate, hydroxypropylmethyl cellulose, Macrogol 400, titanium dioxide. The tablets are coated with (coloured) lacquer. The composition provides for immediate release of quetiapine after oral administration, i.e. the whole bolus is released in the stomach environment.

Quetiapine fumarate is a powder compound with relatively very low density, so that it is very prone for segregation within tabletting processes and direct tabletting is very difficult, if not impossible when high percentages of quetiapine are in the blend.

Furthermore, the therapeutical dose of quetiapine is relatively high. This leads to a need of making compositions with relatively high concentrations of the active (up to 60%). Making tablets of such a high concentration of quetiapine fumarate is difficult, particularly due to the bad tabletting properties of the active.

An advantageous alternative to the immediate release formulation of quetiapine fumarate is a controlled release formulation, preferably exhibiting slow and/or constant release of the drug substance for several hours. Such a formulation can lower the total therapeutical dose that is necessary and/or reduce side effects, can allow for better bioavailability of the drug, and can avoid the need of repeated administration of the drug during a day.

EP 907,364 provides for a sustained release formulation comprising quetiapine and a gelling agent, preferably hydroxypropylmethylcellulose.

WO 2005-041935 provides for a sustained release formulation comprising quetiapine and a wax material.

Although sustained release compositions with quetiapine fumarate are suggested in the art, an alternative sustained or controlled release dosage form would be advantageous.

SUMMARY OF THE INVENTION

The present invention relates to a pharmaceutical composition comprising:

(i) quetiapine or a pharmaceutically acceptable salt thereof, especially quetiapine fumarate;
(ii) a mixed excipient comprising an intimate admixture of polyvinylacetate and polyvinylpyrrolidone in a weight ratio from 5:2 to 10:2; and, optionally
(iii) an acid especially fumaric acid.

The composition is conveniently an oral tablet. The tablet preferably exhibits controlled release meaning that less than 90% is released in 30 minutes in a 0.1 M HCl solution. Typically the tablet provides a release rate complying with at least one of the following characteristics (using Ph.Eur./USP dissolution test):

a) less than 80%, preferably between 30 and 70%, of quetiapine is released in 2 hours when tested in vitro in 0.1 N HCl;
b) 60-100% of quetiapine, in total, is released in 8 hours when the test sub a) is followed by testing in a buffer pH 6.2.

Another aspect of the invention relates to a process for making a controlled release quetiapine tablet, which comprises:

(a) granulating quetiapine or its salt and at least a part of the mixed excipient comprising an intimate admixture of polyvinylacetate and polyvinylpyrrolidone in a weight ratio from 5:2 to 10:2 to form a granulate;
(b) mixing said granulate with one or more additional excipients including optionally an additional portion of said mixed excipient to form a tablet blend; and
(c) compressing said tablet blend into tablets.

A further aspect of the invention relates to a pharmaceutical tablet comprising the above composition and/or made by the above process, wherein the amount of the quetiapine fumarate is from 50 to 600 mg, calculated as quetiapine base.

DETAILED DESCRIPTION OF THE INVENTION

The present invention provides a pharmaceutical composition that is based on a mixture of quetiapine or its pharmaceutically acceptable salt, typically quetiapine fumarate, and a mixed excipient. The mixed excipient comprises an intimate mixture of polyvinylacetate and polyvinylpyrrolidone. The composition can be compressed into tablets having controlled or sustained release properties.

Quetiapine and its salts such as quetiapine fumarate are known compounds. It is used as a solid in the composition of the invention. The solid may comprise any of the crystalline polymorphic modifications thereof as well as the amorphous product, as well as mixtures thereof.

The relative amount of quetiapine and/or its salt such as quetiapine fumarate in the composition may be from 10 to 80 weight % and is preferably from 20 to 60 weight %, expressed in terms of the weight of the free base. As the absolute amount of quetiapine or its salt in the final tablet increases, e.g. 300-600 mg, the lower limit of the percentage of quetiapine or its salt likewise increases in order to keep the tablet a manageable size for oral administration. Thus for higher absolute amounts, it is not uncommon for the quetiapine to be at least 40% or even at least 50% of the tablet weight. Higher loading amounts are more efficient and create a smaller sized tablet but can lead to unacceptable or impractical tabletting as the amount of binder decreases. Thus the amount of quetiapine or its salt generally does not exceed 80%, and typically is 70% or less. In any event, the relative amount of quetiapine or its salt is conveniently in the range of about 25% or 30% to around 55% or 60%.

The mixed excipient comprises an intimate mixture of polyvinyl acetate and polyvinyl pyrrolidone in a weight ratio of 5:2 to 10:2 and preferably is about 8:2. The intimate mixture is generally formed by dissolving both polymers in a solvent and spray drying the solution to form a solid powder. The average molecular weight of the polyvinylacetate component is preferably about 450,000 and the average molecular weight of the polyvinylpyrrolidone component is preferably about 50,000 (in other terms, having so called K-value of about 30). The average molecular weight of the mixed excipient, expressed in K-value (according to Ph.Eur. and USP monograph "Povidone") is preferably about 60-65.

The mixed excipient can contain additional components such as up to 2% of stabilizers, e.g. sodium lauryl sulfate and/or silica.

The mixed excipient may be made as shown above or may be commercially obtained, e.g. under brand name Kollidon SR of BASF.

The mixed excipient is useful in formulating the composition into tablets. The mixed excipient is generally a free-flowing powder with excellent tabletting properties and has been found to be an effective binder for quetiapine fumarate which has poor tabletting properties as discussed above. The povidone part is soluble in water, while the polyvinylacetate is not soluble, which, in total, makes the excipient water insoluble but porous. Thus the mixed excipient is favorable for making a composition with a slow and/or controlled release of the active substance.

The relative amount of the mixed excipient in the composition of the present invention may be from 20 to 80 weight % and is preferably from 25 to 65 weight %, especially 30-60%. The preferred relative amount is particularly useful in making compositions and tablet formulations with high loading of the quetiapine fumarate, as it allows for sufficiently small, and thus well ingestible, tablets.

The composition preferably comprises an acid, preferably fumaric acid. The addition of fumaric acid is advantageous to increase the solubility of quetiapine fumarate at neutral pH, i.e. in small intestines. Quetiapine fumarate has a pH dependent solubility, with a higher solubility in acid environment (pH 1.0: 35.8 mg/ml, pH 6.2: 4.6 mg/ml). The presence of fumaric acid is generally more desirable when the relative amount of quetiapine fumarate increases as it can serve as a suitable modifier of the release rate. Therefore, other release rate modifiers such as water soluble polymers or low or high molecular weight lipophilic additives may not be necessary even under high loading conditions.

The relative amount of the acid, specifically fumaric acid, in the composition is from 0 to 25 weight %. Typically when present, the acid accounts for at least 1%, more typically at least 2% of the composition. In case when the relative amount of the quetiapine fumarate in the composition is higher than 25%, then, for example, the amount of fumaric acid is typically 2-25%, preferably 5-20%.

In addition the composition may also comprise further excipients such as inert fillers (for instance microcrystalline cellulose, lactose, starch, dicalcium phosphate), lubricants (for instance magnesium stearate, calcium stearate, sodium stearyl fumarate), glidants, colourants etc.

While not necessarily prohibited, water soluble polymers and/or low or high molecular weight lipophilic additives are typically not present in the composition and preferably are not present.

The nature and relative amounts of the above basic components in the composition, as well as the process of combining them into a tablet dosage form, allow for control over the release of the active. By proper combination thereof, the desired release rate from the tablet may be obtained.

Preferably, the tablet releases the active substance in a controlled manner over a period of up to 8 hours or longer, whereby at least 60% of the initial dose is released within 8 hours. In an example, which is not a limiting factor of the present invention, the advantageous release of quetiapine fumarate should be approx. 30-70 weight % in two hours and 60-100 weight % in eight hours in a suitable dissolution test. The release rate may be tested in vitro by conventional pharmacopoeial methods. A useful dissolution test simulates the fate of the composition in the patient's body and thus it advantageously comprises a two-step test:

Dissolution test at 37° C. for 2 hours in 0.1 M HCl followed by testing in a buffer pH 6.2. Such dissolution test may be performed under standard requirements of Ph.Eur/USP, at 50-100 rpm, by basket or paddle method.

Under these testing conditions, the preferred characteristics of the tablet complies with the following requirements:

a) less than 80%, preferably between 30 and 70%, of quetiapine is released in 2 hours; and b) 60-100% of quetiapine is released in 8 hours.

Preferably, the release rate in the buffer pH 6.2 basically corresponds to the zero-order rate.

Preferably, the overall release of quetiapine is about 90% of quetiapine within 10-14 hours using the two-step dissolution test described above.

As apparent from the above, the composition of the present invention is primarily intended to be used for making tablets, although capsules or other solid dosage forms could also be formed. The tablets can be made by conventional techniques including wet granulation or direct compression; e.g., both the wet tabletting process and/or dry tabletting process are suitable for making the tablets. In general, the excellent flowability and compressibility of the mixed excipient makes this excipient particularly suitable for the manufacture of sustained release tablets obtained by direct compression, i.e. by a dry process.

However, it has been observed that the release rate of the quetiapine from the tablet formulation of the invention is generally quicker in cases when the formulation was made by the wet process in comparison with the same formulation formulated by a dry process. To make the release properties more robust and better controllable, it appears that a two-step granulation process is useful for making the tablets of the invention. This process is particularly suitable for the composition with high relative amounts of the quetiapine (30-60% of the total mass), as it maximizes the binding properties of the mixed excipient and allows to modulate the release rate in a most efficient way In the first step, the quetiapine or its salt is granulated with a first amount (5-100%, typically 7-70% of the total amount) of the mixed excipient to form a pre-blend (a granulate). Other excipients may also be present in the granulate. Water is the preferred liquid for making the granulate. In the second step, the granulate is then mixed with the rest of the mixed excipient, if any, and the other excipients including the acid component, if present, without using a liquid. While it is possible to incorporate the acid into the granulate, it is generally advisable to incorporate the acid as part of the extra-granular composition. The mixing and addition of additional excipients can be done in one or more steps.

Finally, the tablet formulation is compressed into tablets by conventional methods. The compression force and/or the hardness of the tablet may also affect the overall release rate so it should be properly selected. For instance, the preferred hardness of the tablet of 50 mg strength is from 50 to 150 N, for the 150 mg strength the preferred hardness is from 80 to 150 N and for the 200-400 mg strength the preferred hardness is 80-200 N.

The relative amounts of the mixed excipient used both inter-granular and extra-granular may thus be well controlled and adjusted so that the desired release rate may be obtained by fine tuning these ratios.

The tablet formulated from the composition of the present invention may preferably comprise from 50 to 600 mg of quetiapine fumarate, such as 50, 100, 200, 300, and 400 mg, calculated as the free base. The total weight of the tablet is generally from 150 to 1500 mg.

The tablets may be coated by a conventional film-coat to improve the handling properties thereof.

EXAMPLES

Example 1

Quetiapine Fumarate 50 Mg Strength Tablets by Direct Compression Composition

|  | *02 (mg) | *02 (%) |
|---|---|---|
| Quetiapine fumarate | 57.58 | 28.79 |
| Kollidon SR | 104.86 | 52.43 |
| Fumaric acid | 33.56 | 16.78 |
| magnesium stearate | 4 | 2 |
| Total mass tablet | 200 | — |
| Tablet hardness | 100 | — |
| Tablet diameter | 8 | — |

Process:

Fumaric acid and magnesium stearate were sieved over a 0.8 mm sieve. Quetiapine fumarate, Kollidon SR and fumaric acid were mixed for 15 minutes at 22 rpm in a free fall mixer. Magnesium stearate was added and the blend was mixed for another 5 minutes. The blend was compressed into a tablet with tablet mass 200 mg, tablet diameter 8 mm and hardness 100 N.

Example 2

Quetiapine Fumarate 400 Mg Strength Tablets by a Two Step Granulation Process Composition

|  | **01 (mg) | **01 (%) | **02 (mg) | **02 (%) | **03 (mg) | **03 (%) |
|---|---|---|---|---|---|---|
| Inter granular |  |  |  |  |  |  |
| Quetiapine fumarate | 460.54 | 50 | 460.54 | 50 | 460.54 | 50 |
| Kollidon SR | 41.45 | 4.5 | 82.90 | 9 | 216.45 | 23.5 |
| Extra granular |  |  |  |  |  |  |
| Kollidon SR | 308.56 | 33.5 | 267.11 | 29 | 133.56 | 14.5 |
| Fumaric acid | 92.11 | 10 | 92.11 | 10 | 92.11 | 10 |
| magnesium stearate | 18.42 | 2 | 18.42 | 2 | 18.42 | 2 |
| Total mass tablet | 921.08 | — | 921.08 | — | 921.08 | — |
| Tablet hardness | 175 | — | 175 | — | 175 | — |
| Tablet diameter | 14 | — | 14 | — | 14 | — |

Process:

Quetiapine fumarate and the first part of the Kollidon SR were mixed in the 900 ml bowl with an impellor speed of 300 rpm and a chopper speed of 1000 rpm for 2 minutes. With the same mixing speed water was added with 7 ml/min until a granulate was formed. The granulate was dried overnight in an oven at 60° C. The granulate was continuously milled until it passed a 0.85 mm sieve. Kollidon SR and fumaric acid were added to the milled granulate and mixed for 15 minutes at 22 rpm. Magnesium stearate was passed through a 0.8 mm sieve and added to the blend. The blend was mixed in the turbula for 5 minutes at 22 rpm and compressed into tablets with tablet mass 921 mg, tablet diameter 14 mm and hardness 175N.

Example 3

Quetiapine Fumarate 400 Mg Strength Tablets by a Wet Granulation Process Composition

|  | **04 (mg) | **04 (%) |
|---|---|---|
| Quetiapine fumarate | 460.54 | 50 |
| Kollidon SR | 350 | 38 |
| Fumaric acid | 92.11 | 10 |
| magnesium stearate | 18.42 | 2 |
| Total mass tablet | 921.08 | — |
| Tablet hardness | 175 | — |
| Tablet diameter | 14 | — |

Process:

Quetiapine fumarate and Kollidon SR were mixed in the 900 ml bowl with an impellor speed of 300 rpm and a chopper speed of 1000 rpm for 2 minutes. With the same mixing speed water was added with 7 ml/min until a granulate was formed. The granulate was dried overnight in an oven at 60° C. The granulate was continuously milled until it passed a 0.85 mm sieve. Fumaric acid was added to the milled granulate and mixed for 15 minutes at 22 rpm. Magnesium stearate was passed through a 0.8 mm sieve and added to the blend. The blend was mixed in the turbula for 5 minutes at 22 rpm and compressed into tablets with tablet mass 921 mg, tablet diameter 14 mm and hardness 175N.

Each of the patents, patent applications, and journal articles mentioned above are incorporated herein by reference. The invention having been described it will be obvious that the same may be varied in many ways and all such modifications are contemplated as being within the scope of the invention as defined by the following claims.

I claim:

1. A pharmaceutical composition comprising a mixture of:
   (i) quetiapine or a pharmaceutically acceptable salt thereof;

(ii) a mixed excipient comprising an intimate admixture of polyvinylacetate and polyvinylpyrrolidone in a weight ratio from 5:2 to 10:2; and, (iii) an acid, wherein said acid is contained in amount of 2-25% and is fumaric acid.

2. The composition according to claim 1, wherein said quetiapine or its salt is quetiapine fumarate.

3. The composition according to claim 1, wherein said quetiapine or its salt is contained in an amount of 10-70% of the total mass of the composition.

4. The composition according to claim 3, wherein said quetiapine or its salt is contained in an amount of 20-60% of the total mass of the composition.

5. The composition according to claim 1, wherein said mixed excipient is contained in an amount of 20-80% of the total mass of the composition.

6. The composition according to claim 5, wherein said mixed excipient is contained in an amount of 25-65% of the total mass of the composition.

7. The composition according to claim 6, wherein said mixed excipient is contained in an amount of 30-60% of the total mass of the composition.

8. The composition according to claim 7, wherein said mixed excipient has a weight ratio of polyvinylacetate to polyvinylpyrrolidone of about 8:2.

9. The composition according to claim 8, wherein said polyvinylacetate in said mixed excipient has an average molecular weight of about 450,000.

10. The composition according to claim 9, wherein said polyvinylpyrrolidone in said mixed excipient has an average molecular weight of about 50,000.

11. The composition according to claim 10, wherein said mixed excipient has an average molecular weight expressed in K-value within the range of about 60-65.

12. The composition according to claim 1, wherein said fumaric acid is contained in amount of 5-20%.

13. The composition according to claim 1, which is an oral tablet.

14. The composition according to claim 13, wherein said quetiapine or its salt is contained in an amount of 50-600 mg.

15. The composition according to claim 14, wherein said tablet exhibits an in vitro dissolution profile such that not more than 80%, of said quetiapine or its salt is released in 2 hours in 0.1 M HCl.

16. The composition according to claim 15, wherein said tablet exhibits an in vitro dissolution profile such that 30-70% of said quetiapine or its salt is released in 2 hours in 0.1 M HCl.

17. The composition according to claim 16, wherein said dissolution profile further includes release of 60-100% of said quetiapine or its salt at 8 hours when said 2 hours in 0.1 M HCl is followed by testing in phosphate buffer at pH 6.2.

* * * * *